US012773527B1

(12) United States Patent
Jore

(10) Patent No.: US 12,773,527 B1
(45) Date of Patent: Oct. 27, 2026

(54) SYSTEM AND METHOD FOR REGULATING URINARY FLOW IN A CATHETERIZED USER

(71) Applicant: Bernadine Jore, Apopka, FL (US)

(72) Inventor: Bernadine Jore, Apopka, FL (US)

( * ) Notice: Subject to any disclaimer, the term of this patent is extended or adjusted under 35 U.S.C. 154(b) by 0 days.

(21) Appl. No.: 19/237,384

(22) Filed: Jun. 13, 2025

(51) Int. Cl.
*A61M 25/00* (2006.01)
*A61M 27/00* (2006.01)

(52) U.S. Cl.
CPC ..... *A61M 25/0075* (2013.01); *A61M 25/0017* (2013.01); *A61M 27/008* (2013.01); *A61M 2205/18* (2013.01)

(58) Field of Classification Search
CPC ........ A61F 5/453; A61F 5/455; A61F 5/4553; A61M 25/0017; A61M 25/003; A61M 25/0075; A61M 27/008
See application file for complete search history.

(56) References Cited

U.S. PATENT DOCUMENTS

| | | | | |
|---|---|---|---|---|
| 5,929,747 A * | 7/1999 | Rosenblatt | A61F 5/48 340/573.5 |
| 7,037,303 B2 | 5/2006 | Beaufore et al. | |
| 7,821,873 B2 * | 10/2010 | Carley | G04G 13/026 368/9 |
| 10,342,412 B2 | 7/2019 | Tycast et al. | |
| 11,654,042 B2 * | 5/2023 | Hughett, Sr. | A61F 5/4404 600/581 |
| 12,042,607 B2 * | 7/2024 | Miller | A61M 25/0097 |
| 2014/0180260 A1 | 6/2014 | Mueller | |
| 2019/0126006 A1 * | 5/2019 | Rehm | A61B 10/007 |
| 2019/0216401 A1 * | 7/2019 | Brody | A61M 25/10185 |
| 2023/0106221 A1 | 4/2023 | Meyers et al. | |
| 2024/0058520 A1 * | 2/2024 | Yin | A61F 5/4404 |

* cited by examiner

*Primary Examiner* — Catharine L Anderson
(74) *Attorney, Agent, or Firm* — Dale J. Ream

(57) ABSTRACT

A system for regulating urinary flow in a catheterized user includes a catheter device having an insertion tip for fluid communication with a bladder when in use, the catheter device including tubing coupled at one end to the insertion tip at another end. Further, a flow control mechanism is coupled to a distal end of the tubing that is pivotally movable between a closed configuration blocking a flow of urine and an open configuration allowing the urine to flow through the tubing. The system includes a bladder training support module that includes a mobile application having a timing interface configured to indicate scheduled intervals for actuation of the flow control mechanism, a physical interface configured to provide tactile or visual cues corresponding to bladder training intervals, and a recording element for tracking the timing and duration of valve openings over a defined period of time.

5 Claims, 6 Drawing Sheets

SYSTEM AND METHOD FOR REGULATING URINARY FLOW IN A CATHETERIZED USER

BACKGROUND OF THE INVENTION

This invention relates generally to medical devices and methods and, more particularly, to a system and method for regulating urinary flow in a catheterized user. Specifically, the present invention allows a catheterized user, particularly a user having a mobility disability, to delay urination safely and without a collection bag.

Individuals with certain physical disabilities—particularly those with neurological or neuromuscular conditions such as multiple sclerosis, spinal cord injury, Parkinson's disease, stroke, muscular dystrophy, or other disorders affecting mobility and bladder function—often rely on indwelling catheters, such as Foley or suprapubic catheters, to manage urinary elimination. While these catheters provide reliable bladder drainage, they are typically connected to external collection bags, which can be inconvenient, uncomfortable, and socially limiting—especially during activities requiring prolonged immobility, such as air travel.

Air travel presents a particular challenge for catheterized individuals with limited mobility. Commercial airplane cabins are often cramped, and restrooms may be inaccessible during significant portions of the flight due to turbulence, boarding and landing procedures, or the passenger's own physical limitations. For a person with a suprapubic catheter, the inability to ambulate to a restroom, combined with the need to discreetly manage urinary output, creates a substantial barrier to travel.

Additionally, prolonged passive drainage through a catheter into a collection bag can interfere with bladder function over time. Continuous drainage prevents natural filling cycles, which can lead to reduced bladder tone and capacity. In contrast, bladder training techniques—such as scheduled voiding and voluntary urine retention—have been shown to promote healthier bladder function by increasing bladder volume tolerance and improving continence management.

There remains a need for a catheter system that does not rely on a urine collection bag and that enables the intentional regulation of urine flow. Such a system would not only accommodate the physical limitations of a catheterized individual during air travel or similar long-duration seated activities but also support bladder training principles by allowing scheduled urine release. The present invention addresses this unmet need by providing a catheter system and method that allows a user to delay urination safely and reliably during extended periods of immobility, such as while traveling by air, and that promotes controlled voiding at selected intervals, without requiring access to a restroom, thereby enhancing independence, dignity, and mobility for individuals with disabilities.

SUMMARY OF THE INVENTION

Accordingly, a system and method is proposed that enables the user to intentionally delay urination and regulate voiding times based on a schedule, rather than relying on continuous drainage into a collection bag. For individuals taking an airplane trip, this functionality allows catheterized and disabled users to remain seated and avoid restroom use during the flight, enhancing privacy, dignity, and mobility independence.

In an aspect, the system for regulating urinary flow in a catheterized user includes a catheter device that has an insertion tip that is configured for fluid communication with a bladder when in use, the catheter device including tubing having a proximal end coupled to the insertion tip and a distal end opposite said proximal end, said tubing having a predetermined length. Further, a flow control mechanism is coupled to the distal end of the tubing, the flow control mechanism having at least one valve or clamp that is configured for user-actuated movement between (1) a closed configuration blocking a flow of urine through the tubing, and (2) an open configuration allowing the urine to flow through the tubing.

The system includes a bladder training support module that may include a timing interface configured to indicate scheduled intervals for actuation of the flow control mechanism, a physical interface configured to provide tactile or visual cues corresponding to bladder training intervals, and a recording element for tracking the timing and duration of valve openings over a defined period of time. Operation of the flow control mechanism in accordance with the cues from the bladder training support module is configured to promote increased urine retention time and increased bladder capacity.

Therefore, a general object of this invention is to provide a system for regulating urinary flow in a catheterized user that enables the user to intentionally delay urination and regulate voiding times based on a schedule, rather than relying on continuous drainage into a collection bag.

Another object of this invention is to provide a system for regulating urinary flow in a catheterized user, as aforesaid, that includes a catheter device that has an insertion tip configured for fluid communication with a bladder, tubing coupled to the insertion tip, and a flow control mechanism having at least one valve or clamp configured for user-actuated movement between a closed configuration blocking urine flow through the tubing and an open configuration allowing the urine to flow through the tubing.

Still another object of this invention is to provide a system for regulating urinary flow in a catheterized user, as aforesaid, that includes a bladder training support module that may be implemented via a mobile computing device and programming adapted to train a user regarding bladder techniques for use with the catheter device.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

A system and method for regulating urinary flow in a catheterized user according to a preferred embodiment of the present invention will now be described with reference to the accompanying drawings. More particularly, the following description sets forth a preferred embodiment of a catheter system and method for regulating urinary flow in a catheterized individual.

The system and method is particularly designed to meet the needs of individuals with limited mobility, such as those with neurological and neuromuscular disorders (e.g., multiple sclerosis, Parkinson's disease, spinal injury, stroke, muscular dystrophy), who rely on indwelling catheters and require the ability to control urinary flow during extended periods of immobility, such as during air travel. This system is specifically designed to be used without a urine collection bag, enabling intentional urine retention and timed voiding. It is understood that intentional urinary retention and timed voiding has some advantages over continual urinary drainage and collection that is traditionally associated with indwelling catheterization.

Figure 1:
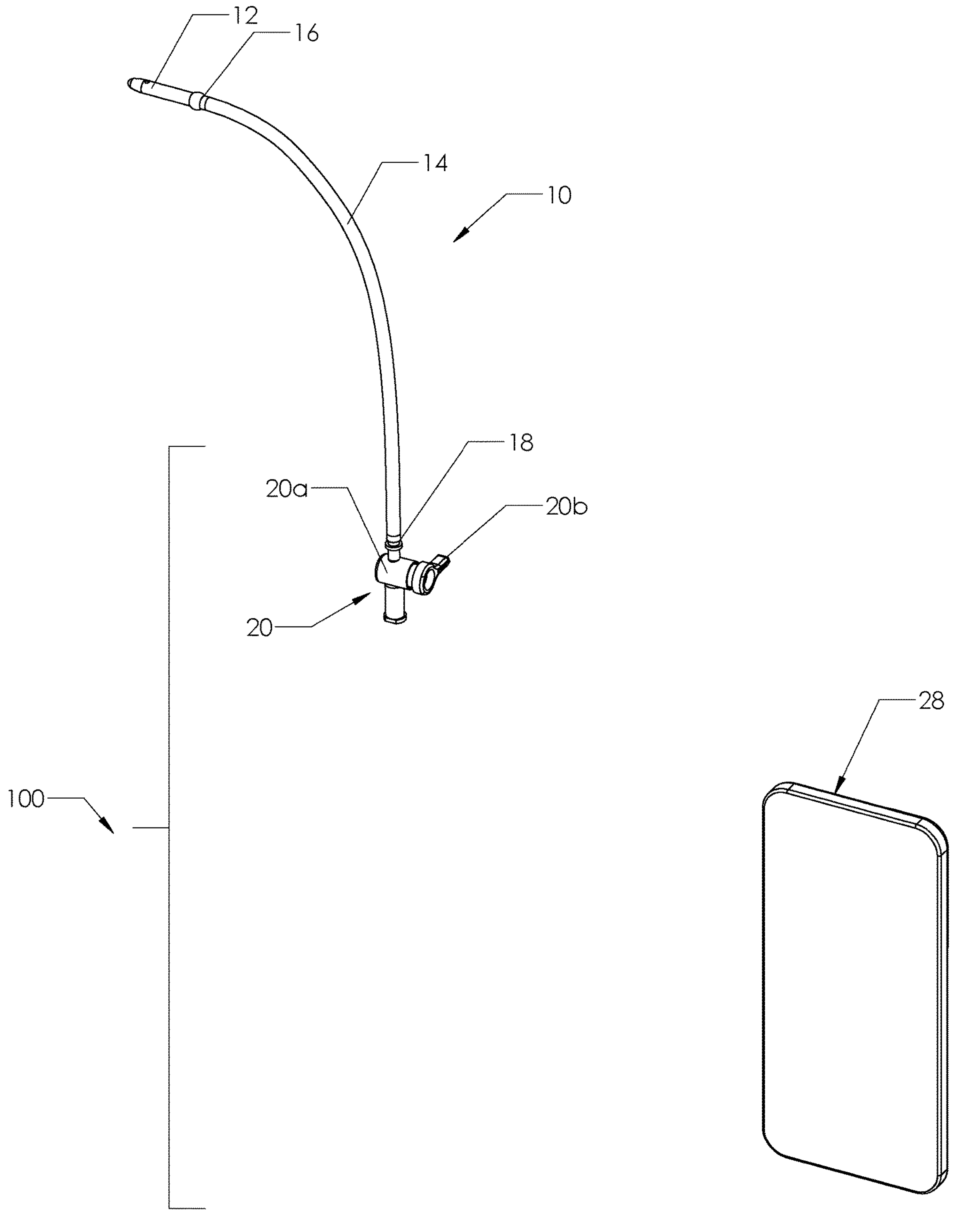
FIG. 1 is a perspective view of a system for regulating urinary flow in a catheterized user according to the present invention.
Figure 2:
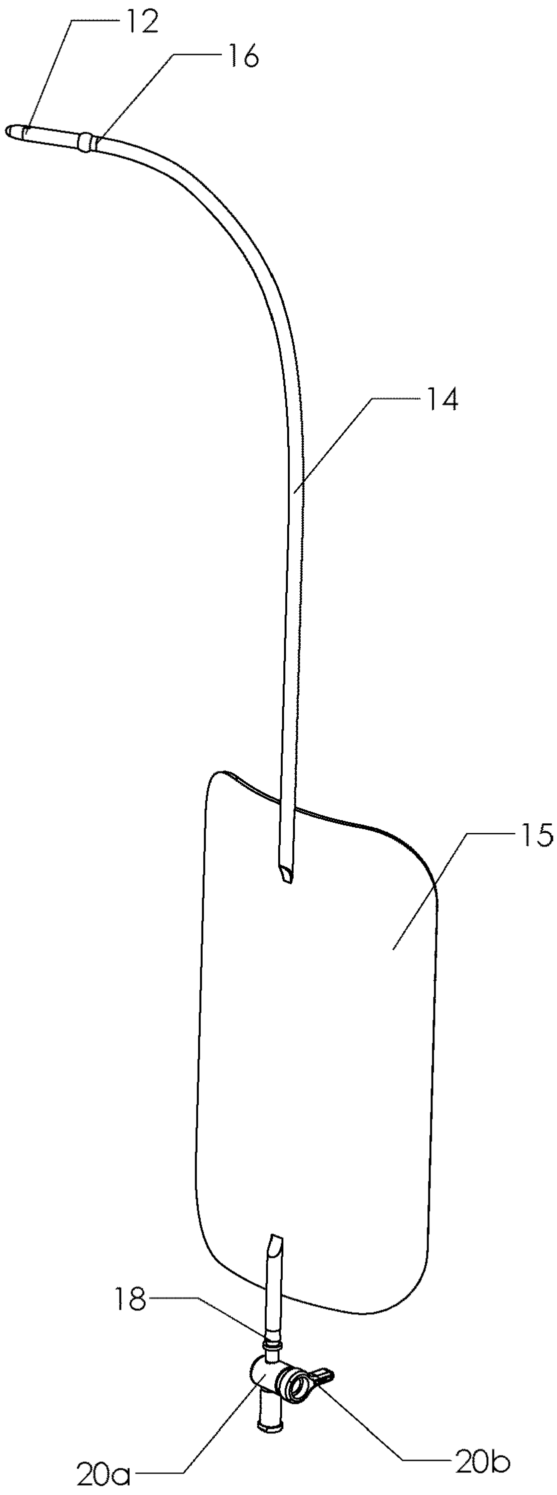
FIG. 2 is a perspective view of a suprapubic catheter with a collection bag illustrated according to the prior art.

Referring now to the embodiment illustrated in FIG. 1, the system 100 includes a catheter device 10 configured for placement in a patient. For instance, the catheter device 10 may be a Foley catheter that is configured for placement in the urethra of a patient or may be a suprapubic tube catheter that is configured for placement through a surgical hole formed in an abdomen of a patient and is in fluid communication with the patient's bladder. In general, the catheter device 10 may include an insertion tip 12 that is configured for fluid communication with the user's bladder. More particularly, the catheter device may be a Foley catheter or a suprapubic catheter, with a predetermined length of flexible tubing 14 having a proximal end 16 connected to the insertion tip 12 and a distal end 18 extending externally from the patient. The tubing 14 may have a predetermined length and diameter—as may be appropriate to respective circumstances. Traditionally, and indwelling catheter system is characterized by the tubing being connected to a collection bag 15 in a configuration as shown in FIG. 2. Removing the collection bag 15 from the catheter system as is proposed in the present invention is unexpected as it invites a user having urinary accidents. How this is avoided will be described in more detail below.

A flow control mechanism 20 is operably connected to the distal end 18 of the tubing 14. The flow control mechanism 20 comprises a valve or clamp that can be manually or electromechanically actuated between:

- a closed configuration, which blocks fluid flow through the catheter tubing, thereby allowing urine to accumulate in the bladder or inside the tubing 14 upstream of the flow control mechanism 20, and
- an open configuration, which allows urine to exit through the distal end 18 of the tubing 14 when voiding is desired.

The valve or clamp is preferably designed to be secure against inadvertent activation, with tactile feedback or detent mechanisms that prevent accidental opening-particularly important in the constrained and jostling environment of commercial air travel. In other words, the flow control mechanism 20 may include a lever configured for pivotal manipulation by a user.

Figure 3A:
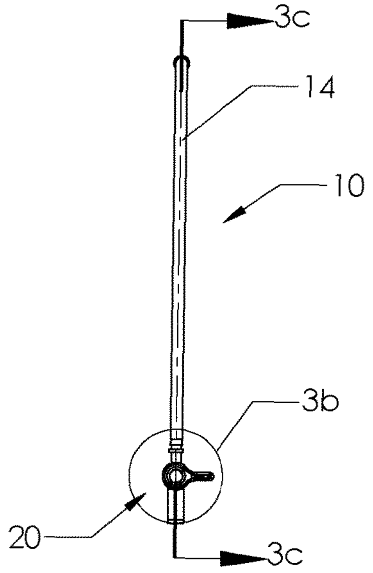
FIGS. 3*a* to 3*d* are isolated and sectional views of a Luer lock fluid valve according to the present invention illustrated in a closed configuration.
Figure 3C:
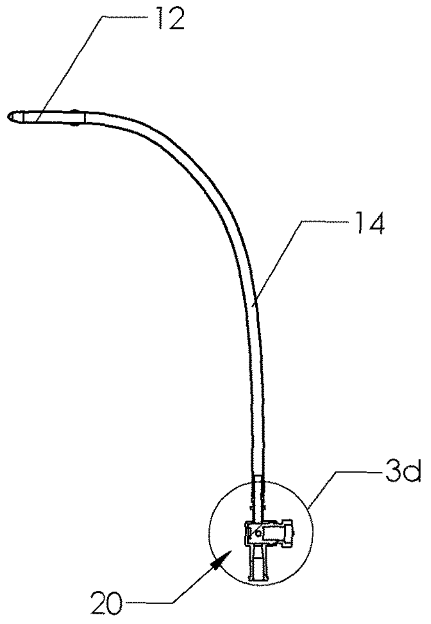
Figure 3B:
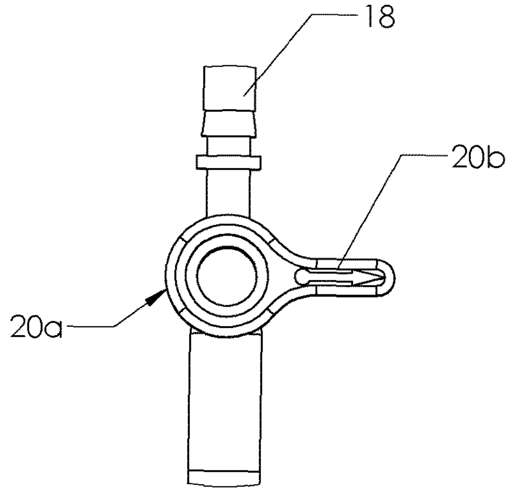
Figure 3D:
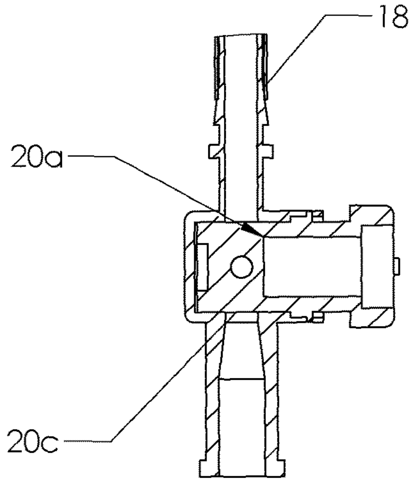
Figure 4A:
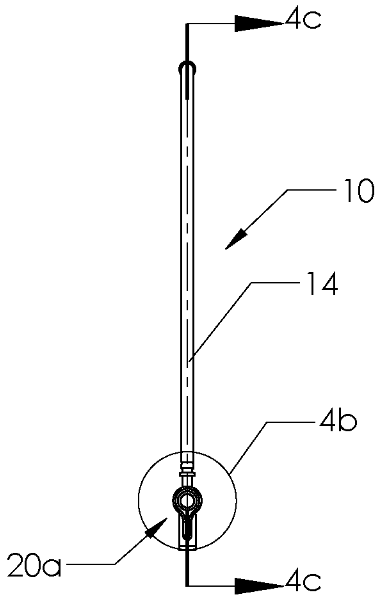
FIGS. 4*a* to 4*d* are isolated and sectional views of a Luer lock fluid valve according to the present invention illustrated in an open configuration.
Figure 4C:
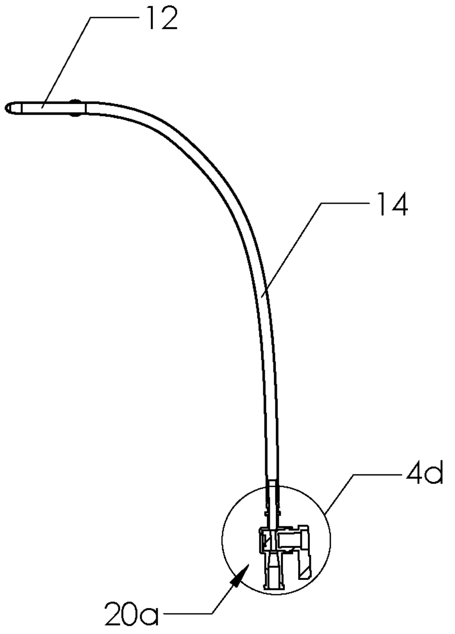
Figure 4B:
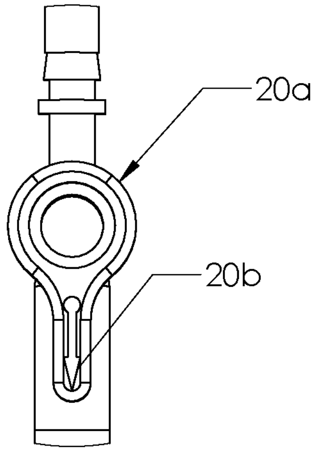
Figure 4D:
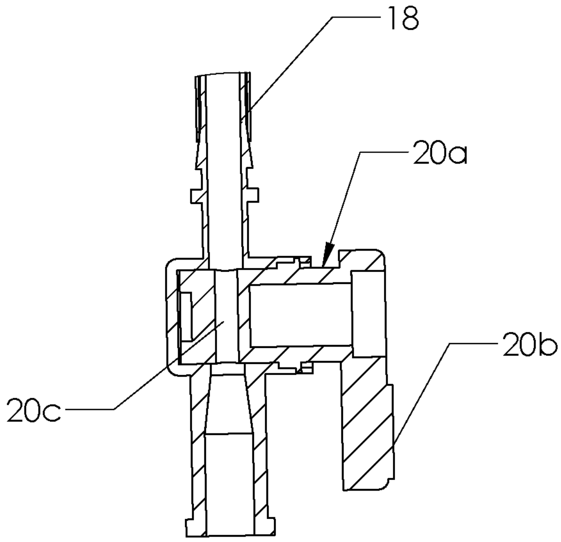

For the sake of clarity, multiple types of flow control mechanisms 20 are illustrated in the accompanying illustrations. In one embodiment, the flow control mechanism 20 may be a Luer lock valve 20*a* which includes a tactile lever 20*b* that may be rotatably manipulated to either block a channel 20*c* and thus block urine flow or unblock the channel 20*c*, respectively. accordingly, fluid is blocked from flowing through the valve illustrated in FIG. 3*d* whereas fluid is allowed to flow through the valve illustrated in FIG. 4*d*.

Figure 5A:
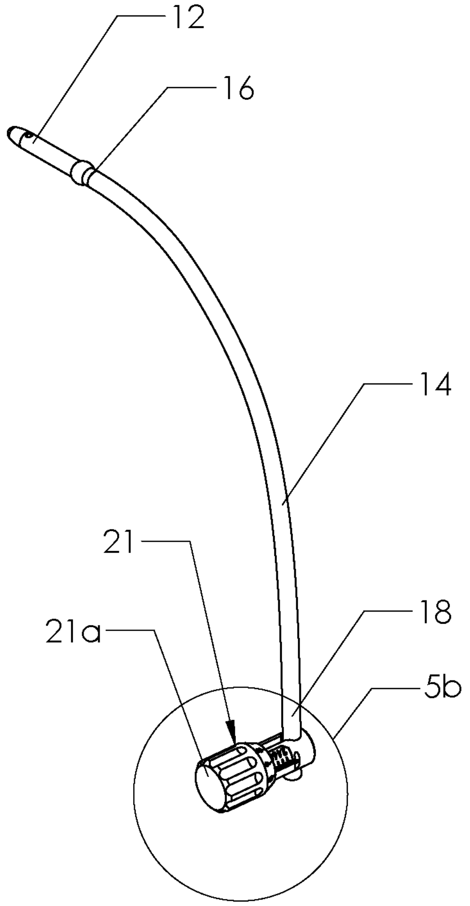
FIG. 5*a* is a perspective view of the present system in use with a pinch valve.
Figure 5B:
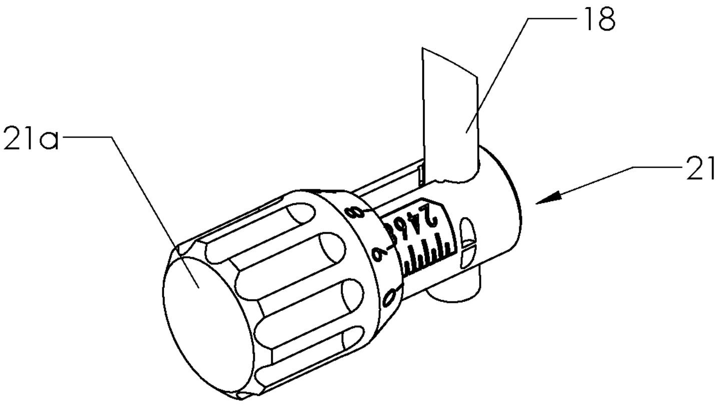
FIG. 5*b* is an isolated view on an enlarged scale taken from FIG. 5*a;*

In an embodiment shown in FIGS. 5*a* and 5*b*, the flow control mechanism 20 is illustrated as a pinch valve 21, the pinch valve having a rotatable knob 21*a* for tightening against (i.e., pinching) the tube or be loosened to allow a fluid flow therethrough.

In the preferred embodiment, the system 100 includes a bladder training support module 30, implemented via a digital or analog interface, such as computer software stored and running on a computing device 28 such as a mobile phone. In an embodiment, the computing device 28 may include a processor 31 in data communication with a non-transient memory 32 that is configured for storing programming 32*a* and data. This module 30 assists the user in maintaining a schedule for opening and closing the valve, supporting bladder training by extending intervals between urination and encouraging increased bladder capacity.

Figure 6A:
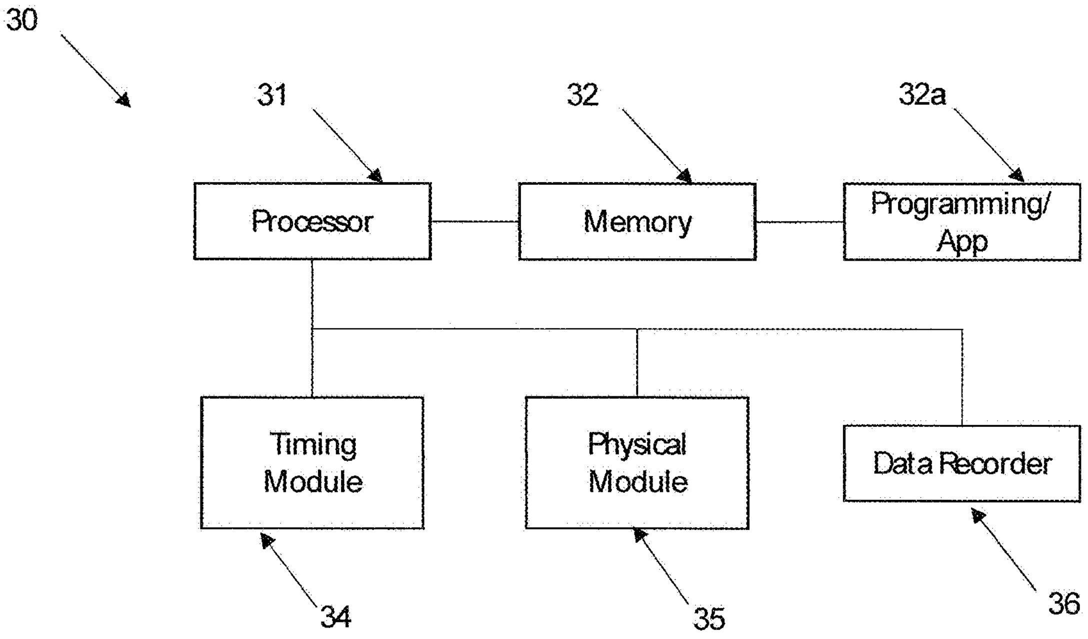
FIG. 6*a* is a block diagram illustrating the electronic components of the system according to the present invention.

As shown in FIG. 6*a*, the bladder training support module 30 may include:

- A timing interface 34, such as a digital display or mobile app, configured to alert the user at preset intervals for scheduled voiding;
- A physical interface 35, such as an LED indicator, haptic signal, or vibrating alert, to provide discreet reminders to operate the flow control mechanism 20;
- A data recording element 36, which tracks the time and duration of each valve opening, allowing progress monitoring over time.

The timing interface 34 may be programmable or automatically adaptive, modifying interval lengths based on historical user data to gradually increase bladder retention periods in a controlled manner. In other words, the timing interface 34 may include predetermined method steps for energizing an audible alarm, the visual alert (LED indicator), vibrator motor, or the like, or may be set up initially by the user and is in electrical communication with the timing interface 34. This data may be saved and stored in memory and executed by the processor 31. Similarly, analytics and data generated by the data recording element 36 may be stored in memory and published to the display of the computing device 28.

Figure 6B:
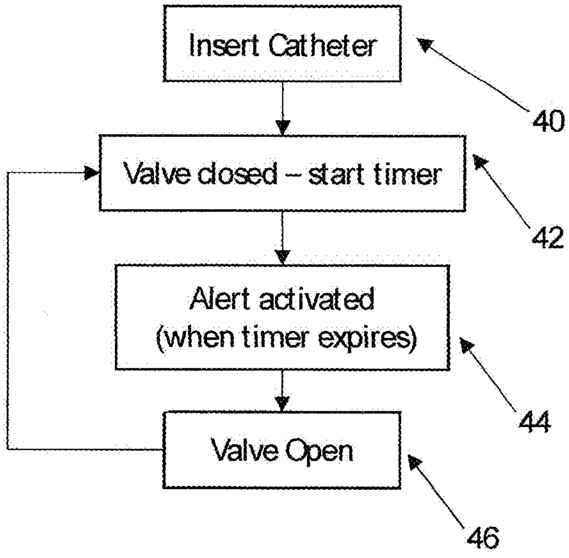
FIG. 6*b* is a flowchart of a method for using the catheter system according to the present invention.

In operation, the catheter system is used as follows (as shown in FIG. 6*b* and delineated by reference characters 40 to 46, respectively):

1. A caregiver or user inserts the catheter device (shown at step 40) such that the insertion tip 12 is in communication with the bladder. It is understood that this may describe a procedure best performed by a doctor, nurse, or by the user.
2. The distal end of the tubing remains external and is coupled directly to the flow control mechanism 20 (omitting the traditional collection bag).
3. During routine use, the valve is maintained in a closed configuration 42, allowing urine to collect in the bladder.

4. At scheduled intervals—defined by the bladder training support module 30 or set by the user—an alert may sound 44 and the flow control mechanism 20 is manually or electronically opened 46, allowing the bladder to empty through the tubing 14.
5. The flow control mechanism 20 is then closed again 42, restarting the retention interval.

This method enables the user to intentionally delay urination and regulate voiding times based on a schedule, rather than relying on continuous drainage into a collection bag. For individuals taking an airplane trip, this functionality allows catheterized and disabled users to remain seated and avoid restroom use during the flight, enhancing privacy, dignity, and mobility independence.

The action of bladder training implemented by the bladder training module 30 may integrate and implement the scholarship known in the art. For instance, to train intentional bladder retention or slow down bladder flow, one can use methods like bladder training, pelvic floor exercises, and lifestyle modifications. Bladder training may include scheduled voiding which, by definition, includes the steps of going to the bathroom at scheduled times whether a person feels an urge or not as a means for training one's bladder to hold more urine and reduce frequency. Similarly, there is delayed voiding which includes gradually increasing the time between bathroom visits by resisting the urge to urinate for short periods of time. Urge suppression may include using relaxation techniques, deep breathing, or distraction methods. Is understood that these methods may be presented visually by the app on demand when the app is initiated by a user.

Bladder training also utilizes training exercises such as Kegel exercises that strengthen the pelvic floor muscles that support the bladder and urethra. More particularly, Kegel exercises target muscles that are used to stop urine midstream and then to squeeze, hold, and relax them in regular cycles. Regular practice is key throughout the day.

Yet another technique for bladder training is to drink fluids in smaller quantities, especially before bedtime. Further, one should reduce or eliminate bladder irritants like caffeine, alcohol, and spicy foods. One should ensure a balanced diet with fiber-rich foods to prevent constipation, which can put pressure on the bladder.

Above all, the app may be programmed to publish that it is advisable to consult with a healthcare provider or pelvic floor therapist before starting any bladder training or exercise program, especially if the user has any underlying health conditions. Further, a user should gradually increase the time between voids and the intensity of exercises and consistency is key.

The catheter system may optionally include antimicrobial materials or hydrophobic coatings on the valve or tubing to reduce the risk of infection. Additionally, the flow control mechanism may be designed with tamper-resistant features for use in institutional care settings or for pediatric patients. In another variation, the bladder training support module may integrate with a smartphone application to provide customizable alerts, logging, and even remote caregiver monitoring of adherence to a voiding schedule.

In use, the system is particularly well-suited for individuals with permanent or temporary mobility impairments, including those with:

Multiple sclerosis,
Spinal cord injuries,
Stroke,
Parkinson's disease, or
Other neurogenic bladder or neuromuscular disorders.

It is understood that while certain forms of this invention have been illustrated and described, it is not limited thereto except insofar as such limitations are included in the following claims and allowable functional equivalents thereof.

What is claimed is:

1. A method for regulating urinary flow in a catheterized user, the method comprising:

providing a catheter device having an insertion tip configured for fluid communication with a bladder, the catheter comprising a predetermined length of tubing with a proximal end coupled to the insertion tip and a distal end coupled to a flow control mechanism, wherein the catheter device is configured for use without a urine collection bag;

configuring the flow control mechanism to transition between a closed configuration and an open configuration;

maintaining the flow control mechanism in the closed configuration during scheduled retention intervals so as to intentionally retain urine within the bladder for bladder conditioning;

operating the flow control mechanism in accordance with a predetermined schedule stored in a bladder training support module to permit scheduled voiding events; and monitoring usage data corresponding to the intervals between transitions of the flow control mechanism, wherein the schedule is adapted over time to progressively increase urine retention intervals to promote increased bladder capacity.

2. The method of claim 1, further comprising adjusting the schedule based on compliance data or historical retention performance recorded by the bladder training support module.

3. The method of claim 1, wherein the flow control mechanism includes a tactile interface configured to resist accidental opening during air travel or prolonged periods of seated inactivity.

4. The method of claim 1, wherein the catheter device is a suprapubic catheter configured to be retained in place for continuous bladder access during extended periods without a collection bag.

5. The method of claim 1, wherein the bladder training support module further includes instructional content related to behavioral exercises to support bladder capacity improvement.

* * * * *